United States Patent [19]
Wolfram

[11] Patent Number: 4,532,345
[45] Date of Patent: Jul. 30, 1985

[54] PROCESS FOR PREPARING ARYLOXYALKYLPYRUVIC ACIDS

[75] Inventor: Joachim W. Wolfram, Baton Rouge, La.

[73] Assignee: Ethyl Corporation, Richmond, Va.

[21] Appl. No.: 529,570

[22] Filed: Sep. 6, 1983

[51] Int. Cl.$^3$ .............................................. C07C 51/12
[52] U.S. Cl. .................................. 562/406; 562/464; 562/462
[58] Field of Search ........................ 562/406, 464, 462

[56] References Cited

U.S. PATENT DOCUMENTS 4,152,352  5/1979  Perron .................................. 562/406

Primary Examiner—Paul J. Killos
Attorney, Agent, or Firm—Donald L. Johnson; John F. Sieberth; John F. Hunt

[57] ABSTRACT

A process for the production of aryloxyalkylpyruvic acid of the general formula:

$(R)_n-A-O-(CR'_2)_m-CR''H-COCOOH$ wherein:

A represents an aromatic hydrocarbon radical containing 1 or 2 condensed benzene rings, R, R' and R" may be the same or different, and are selected from hydrogen and linear or branched alkyl radicals having up to about 6 carbon atoms, n is 0 or an integer from 1–5 when A contains one benzene ring, and n is 0 or an integer from 1–7 when A contains two condensed benzene rings and m is 0–20, which comprises carbonylating an aryloxyalkyl halide of the general formula:

$(R)_n-A-O-(CR'_2)_m-CR''H-X$ where R, R', R", n, A and m are as defined above and X represents halogen in a liquid solvent medium with carbon monoxide at elevated temperature and elevated pressure in the presence of a catalytic amount of a metal carbonyl compound and an alkali metal inorganic base or an alkaline earth metal inorganic base.

16 Claims, No Drawings

PROCESS FOR PREPARING ARYLOXYALKYLPYRUVIC ACIDS

BACKGROUND

The present invention relates to a process for the carbonylation of aryloxyalkyl halides to form aryloxyalkylpyruvic acids as the predominant product. More particularly, the present invention relates to the carbonylation of aryloxyalkyl halides to form aryloxyalkylpyruvic acids containing in the aromatic part of their molecules a benzene ring which may or may not be substituted or condensed benzene rings which also may or may not be substituted.

The practical value of such α-keto-carboxylic acids is that they are deemed to be useful as intermediates in the preparation of herbicides, insecticides and other chemical products.

It is known in the art to prepare arylpyruvic acids. For example, U.S. Pat. No. 4,152,352 discloses the preparation of an arylpyruvic acid by reacting an arylmethyl halide in a liquid solvent medium with carbon monoxide at pressures of 5 to 200 bars in the presence of a catalytic amount of a metal carbonyl compound and an alkaline earth metal inorganic base. Also, U.K. Patent Application No. 2,026,478A discloses that alkali metal salts of an arylpyruvic acid can be prepared by reacting an arylmethyl halide, carbon monoxide and an alkali metal base in the presence of a metal carbonyl compound as catalyst and in the presence of an alcohol or cyclic ether as solvent.

SUMMARY

It has now been found that aryloxyalkylpyruvic acids of the general formula:

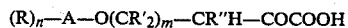

in which:
A presents an aromatic hydrocarbon radical containing 1 or 2 condensed benzene rings, and
R, R' and R", which may be the same or different, represent hydrogen or linear or branched alkyl radicals having up to about 6 carbon atoms, and
n is 0 or an integer from 1–5 when A contains one benzene ring, and n is 0 or an integer from 1–7 when A contains two condensed benzene rings and m is 0–20, can be prepared by carbonylating an aryloxyalkyl halide of the general formula:

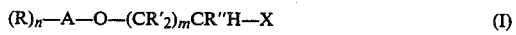

where R, R', R", n, A and m are as defined above and X represents halogen, in a liquid solvent medium, which carbon monoxide at a pressure of from about 300 to 3000 psig in the presence of a catalytic amount of a metal carbonyl compound and an alkali metal inorganic base or an alkaline earth metal inorganic base.

DESCRIPTION OF THE PREFERRED EMBODIMENTS

Specific examples of halides of formula (I) which can be used in the present process include:
2-phenoxyethyl bromide
3-phenoxypropyl bromide
4-phenoxybutyl bromide
5-phenoxypentyl bromide
6-phenoxyhexyl bromide
7-phenoxyheptyl bromide
8-phenoxyoctyl bromide
2-(2-naphthoxy) ethyl bromide
3-(2-naphthoxy) propyl bromide
4-(2-naphthoxy) butyl bromide
5-(2-naphthoxy) pentyl bromide Illustrative examples of α-keto carboxylic acids which can be made by the process of the present invention include:
4-phenoxy-2-oxobutanoic acid
5-phenoxy-2-oxopentanoic acid
6-phenoxy-2-oxohexanoic acid
7-phenoxy-2-oxoheptanoic acid
8-phenoxy-2-oxooctanoic acid
9-phenoxy-2-oxononanoic acid
10-phenoxy-2-oxodecanoic acid
4-(2-naphthoxy)-2-oxobutanoic acid
5-(2-naphthoxy)-2-oxopentanoic acid
6-(2-naphthoxy)-2-oxohexanoic acid
7-(2-naphthoxy)-2-oxo-heptanoic acid The reaction is carried out in the presence of a mixture of water and alcohol as a reaction medium in which carbonylation of the aryloxyalkyl halides takes place. Alcohols which may be employed in the reaction may be straight-chain, branched or cyclic, and preferably contain up to 6 carbon atoms. Methanol, ethanol, propanol, isopropanol, n-butanol, isobutanol, t-butanol, and t-amyl alcohol may be mentioned as examples. Cyclic ethers, such as tetrahydrofuran, also may be used. A particularly preferred solvent alcohol is t-butanol. Mixtures containing about 10% to 90% by weight of water and about 90% to 10% by weight alcohol generally are used. Preferred mixtures contain about 30% to 80% by weight water and about 70% to 20% by weight alcohol.

The reaction takes place in the presence of a basic substance, suitably an alkali metal or an alkaline earth metal hydroxide employing a metal carbonyl compound. Although not wishing to be bound by theory, it is believed that the aryloxyalkyl halide compound undergoes a reaction with the carbon monoxide and basic substance whereby the salt of the aryloxyalkylpyruvic acid is formed from which the aryloxyalkylpyruvic acid is isolated after acidification in a known manner.

Specific examples of suitable basic agents which can be used in the practice of the process include: LiOH, NaOH, KOH, RbOH, Ca(OH)$_2$, Ba(OH)$_2$ and Mg(OH)$_2$. Ca(OH)$_2$ is particularly preferred. Yields of aryloxyalkylpyruvic acids of up to approximately 50% can be obtained using Ca(OH)$_2$ as the basic substance and a solvent medium of t-butanol and water.

The amount of basic agent used can vary within wide limits. In general, the molar ratio of alkali metal base or alkaline earth metal base to aryloxyalkyl halide is preferably approximately 6:1 to 2:1.

In the process described herein, it is preferred to use metal carbonyl compounds as carbonylation catalysts. These catalysts include particularly metal carbonyls such as iron-pentacarbonyl, dicobalt-octacarbonyl and nickel-tetracarbonyl, or their salts such as, for example, the potassium or sodium salts thereof. Dicobalt-octacarbonyl is very particularly suited. These catalysts can be added to the medium in the solid state or in the form of solutions in the solvent used for the carbonylation reaction. The weight ratio of metal carbonyl compound to aryloxyalkyl halide reactant is preferably from about 1:1 to 1:300, and more preferably from about 1:10 to 1:75.

The concentration of the aryloxyalkyl halide reactant of formula (I) used in the reaction solvent is not critical and can vary within wide limits. Thus, it can be between about 1 and 30% by weight, based on the weight of the solvent, however, it is possible to go outside of these limits without disadvantage.

The present process is advantageously carried out by bringing the mixture consisting of the aryloxyalkyl halide, the metal carbonyl catalyst and the alkali metal base or alkaline earth metal base, suspended in a mixture of water and alcohol, into contact in a suitable pressure-resistant reactor equipped with a stirrer, with a large excess of carbon monoxide (amount greater than 2 moles of carbon monoxide per mole of the aryloxyalkyl halide) introduced at the desired pressure and temperature, in accordance with techniques suitable for bringing about the reaction between a liquid phase and a gas phase.

The carbonylation reaction is carried out at a temperature in the range of from about 30° C. to about 150° C., preferably from about 50° C. to 120° C., over a period of time of from about 3 to 60 hours, preferably about 3 to 10 hours.

In general, the reaction takes place at elevated carbon monoxide pressures. Typical elevated pressures are those pressures falling in the range of from about 300 psig to about 3000 psig. Preferably, the reaction takes place at a pressure in the range of about 300 psig to 1000 psig. The carbon monoxide may contain or be mixed with an inert gas, such as nitrogen.

On completion of the reaction, the product mixture is filtered, resulting in the alkali metal salt or alkaline earth metal salt of the aryloxyalkylpyruvic acid being separated from the liquid reaction components as the main solid component, together with a small amount of the alkali metal salt or alkaline earth metal salt of the corresponding aryloxyalkylacetic acid in solid form and co-product aryloxyalkylhydroxy acid. The filtrate contains the remainder of the alkali metal salt or alkaline earth metal salt of the aryloxyalkylacetic acid, unreacted aryloxyalkyl halide and aryloxyalkyl alcohol produced by basic hydrolysis of the starting halide reactant.

In a further process step, the metal salt of the aryloxyalkylpyruvic acid is acidified with a dilute acid, such as hydrochloric acid, so as to displace the aryloxyalkylpyruvic acid from its alkali metal salt or alkaline earth metal salt. The solution obtained is extracted with a suitable solvent, for example, an ether, such as diethyl ether, and the organic extract thus obtained is purified by conventional acid-base work-up. The final residue consists of aryloxyalkylpyruvic acid of good purity.

The reaction filtrate can be treated, if desired to recover the aryloxyalkylacetic acid which it contains. For example, it is possible to free it from the water and the alcohol and, where appropriate, from the unreacted acyloxyalkyl halide which it contains by distillation at atmospheric pressure. After cooling, the mixture can be acidified with an inorganic acid such as hydrochloric acid and the mixture subsequently extracted with a suitable solvent, for example, diethyl ether. The organic extract can then be washed with an aqueous alkaline solution and the aqueous wash solution acidified and extracted to give, after removing the extraction solvent, a residual mixture containing the arylalkyloxyacetic acid.

If desired, lower alkyl esters of the aryloxyalkylpyruvic acid products of the present invention can be prepared by esterifying the aryloxyalkylpyruvic acid product according to conventional esterification techniques employing lower aliphatic alkanol in the presence of acid catalysts such as, for example, $BF_3$, $BF_3 \cdot HCl$, or $BF_3 \cdot MeOH$, $BF_3 \cdot Et_2O$ or diazomethane at suitable reaction conditions.

The following example illustrates the invention.

EXAMPLE 1

13.4 g (50.48 mmoles) of 4-phenoxybutyl bromide, 70 mLs of t-butanol, 1.0 g (2.92 mmoles) of $Co_2(CO)_8$, 30 mLs of $H_2O$, and 17.31 g (234 mmoles) of $Ca(OH)_2$ were charged to a 300 ml autoclave and stirred for 9 hours at 90° C. under approximately 1000 psig CO pressure. The reaction mixture then was cooled to room temperature and filtered. The crude cake was rinsed with 100 mLs of a solution comprised of 50 mLs of water and 50 mLs of t-butanol, to give 28.7 g of an off-white solid. The solid product was acidified with 10% HCl with cooling, extracted with diethyl ether and dried over $MgSO_4$. The solvent was evaporated therefrom to give 7.65 g (62% yield) of crude reaction product. Analysis of the crude product by $^1H$ NMR, gas chromotography and mass spectroscopy showed that the product contained 6-phenoxy-2-oxo-hexanoic acid of 78% purity. Major impurities in the crude product were identified as 5-phenoxy pentanoic acid (10%) and 6-phenoxy-2-hydroxy hexanoic acid (12%).

Having described the process which Applicant regards as his invention, it should be recognized that changes and variations within the scope and spirit of the invention can be made by one skilled in the art and it is accordingly to be understood that the present description of the invention be limited only by the lawful scope of the following claims.

I claim:

1. A process for the production of an aryloxyalkylpyruvic acid of the general formula:

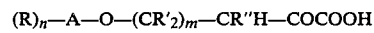

$$(R)_n-A-O-(CR'_2)_m-CR''H-COCOOH$$

or a salt thereof wherein:
A represents a benzene or napthalene group,
R, R' and R" are the same or different, and are hydrogen or a linear or branched alkyl radical having up to 6 carbon atoms,
n is 0 or an integer from 1–5 when A is a benzene group, and n is 0 or an integer from 1–7 when A is a naphthalene group and m is 0–20, which comprises carbonylating an aryloxyalkyl halide of the general formula:

$$(R)_n13\ A-O-(CR'_2)_m-CR''H-X$$

where R, R', R", n, A and m are as defined above and X represents halogen in a liquid solvent medium, with carbon monoxide at elevated temperature and elevated pressure in the presence of a catalytic amount of a metal carbonyl compound and an alkali inorganic base or an alkaline earth metal inorganic base to form a salt of the aryloxyalkylpyruvic acid, and optionally then acidifying the salt to form said acid.

2. The process of claim 1, wherein the products produced by the process are 4-phenoxy-2-oxobutanoic acid, 5-phenoxy-2-oxopentanoic acid, 6-phenoxy-2-oxohexanoic acid, 7-phenoxy-2-oxoheptanoic acid, 8-phenoxy-2-oxooctanoic acid, 9-phenoxy-2-oxononanoic acid, 10-phenoxy-2-oxodecanoic acid, 4-(2-naphthoxy)-2-oxobutanoic acid, 5-(2-naphthoxy)-2-oxopentanoic acid, 6-(2-naphthoxy)-2-oxohexanoic acid, or 7-(2-naphthoxy)-2-oxo-hepanoic acid.

3. The process of claim 1, wherein the carbon monoxide pressure is from about 300 to 3000 psig.

4. The process of claim 1, wherein the reaction is carried out at a temperature of from about 30° C. to about 150° C.

5. The process of claim 1, wherein the inorganic base is LiOH, NaOH, KOH, RbOH, Ca(OH)$_2$, Ba(OH)$_2$ and Mg(OH)$_2$.

6. The process of claim 1, wherein the molar ratio of the inorganic base is from about 2 to 6 moles per mole of aryloxyalkyl halide.

7. The process of claim 1, wherein the metal carbonyl catalyst compound is iron pentacarbonyl, dicobalt-octacarbonyl, or nickel-tetracarbonyl.

8. The process of claim 7, wherein the metal carbonyl is dicobalt-octacarbonyl.

9. The process of claim 7, wherein the metal carbonyl catalyst compound is a salt of iron-pentacarbonyl, dicobalt-octacarbonyl or nickel-tetracarbonyl.

10. The process of claim 9, wherein said salt is sodium or potassium.

11. The process of claim 1, wherein the weight ratio of metal carbonyl compound to aryloxyalkyl halide reactant is from about 1:1 to 1:3000.

12. The process of claim 1, wherein the liquid solvent medium is a mixture of water and alcohol.

13. The process of claim 12, wherein the mixture consists of from about 10% to about 90% by weight water and from about 90% to about 10% alcohol.

14. The process of claim 12, wherein the alcohol is a saturated, linear or branched, aliphatic, monohydroxylic or polyhydroxylic compound containing up to 6 carbon atoms.

15. The process of claim 14, wherein the alcohol is tert-butanol.

16. The process of claim 1 wherein m is 1–20.

* * * * *

UNITED STATES PATENT AND TRADEMARK OFFICE
CERTIFICATE OF CORRECTION

PATENT NO. : 4,532,345
DATED : JULY 30, 1985
INVENTOR(S) : JOACHIM W. WOLFRAM

It is certified that error appears in the above-identified patent and that said Letters Patent is hereby corrected as shown below:

Column 4, line 51, reads "$(R)_n 13 \ A-O-(CR'_2)_m-CR''H-X$" and should read -- $(R)_n-A-O-(CR'_2)_m-CR''H-X$ --.

Signed and Sealed this

Fifteenth Day of October 1985

[SEAL]

Attest:

DONALD J. QUIGG

Attesting Officer

Commissioner of Patents and
Trademarks—Designate